United States Patent
Gürtler et al.

(10) Patent No.: US 6,303,837 B1
(45) Date of Patent: Oct. 16, 2001

(54) PROCESS FOR SYNTHESIZING α-SUBSTITUTED RING SYSTEMS

(75) Inventors: Christoph Gürtler, Köln; Manfred Jautelat, Burscheid, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/387,020

(22) Filed: Aug. 31, 1999

(30) Foreign Application Priority Data

Sep. 3, 1998 (DE) .............................. 198 40 107

(51) Int. Cl.[7] .................................... C07C 35/18
(52) U.S. Cl. .................... 568/825; 568/823; 568/700; 556/136; 540/538; 558/44; 558/45; 558/303
(58) Field of Search ................... 568/825, 823, 568/700; 558/303, 44, 45; 556/136; 540/538; 548/469

(56) References Cited

U.S. PATENT DOCUMENTS

| 4,060,468 | * | 11/1977 | Castner ........................ 204/157.75 |
| 5,312,940 |   | 5/1994  | Grubbs et al. ................... 556/136 |
| 5,922,863 | * | 7/1999  | Grubbs et al. ................... 540/538 |
| 6,077,805 | * | 6/2000  | Van Der Schaaf et al. ........ 502/155 |

FOREIGN PATENT DOCUMENTS

WO 99/00397 * 1/1999 (WO) .

OTHER PUBLICATIONS

Paney et al , Enyne Cyclization by Photoinduced Electron Transfer—: a New Carbocyclization Strategy, Tetrahedron, p 1483–1491, Jan. 1995.*
Angew. Chem. Die Olefinmetathese in der organischen Synthese, Matthias Schuster and Siegfried Blechert, (month unavailable) 1997, 109, pp. 214–2144.
J. Chem. Soc. Perkin Trans, 1, Ring closing diene metathesis in organic synthesis, Susan K. Armstrong, (month unavailable) 1998, pp. 371–388.
K. Weissermel et al. "Industirelle Organische Chemie", 4. Auflage VCH Verlagsgesellschaft Weinheim, 1994, s. 375–379, Oxidations– Und Folgeprodukte des Benzols.
T. Prinz et al., Angew. Chem., 108, (month unavailable) 1996, pp. 1835–1836, Zweiphasenkatalyse: eine Strategie zur Vermeidung von Konsekutivreaktionen am Beispiel der Telomerisation von Butadien und Ammoniak.
K. Kaneda et al, J. Org. Chem. 46, (month unavailable) 1981, pp. 2356–2362, Selective Telomerization of Butadiene with Various Nucleophiles Catalyzed by Polymer–Bound Palladium (0) Complexes.
R.M. Manyik et al, J. Chem. Soc. D.7, (month unavailable) 1971, p. 330, The Palladium Complex–catalysed Synthesis of Octadienols from Butadiene and Water.
M.T. Crimmins et al, J. Org. Chem. 61, (month unavailable) 1996, pp. 4192–4193, An Efficient Asymmetric Approach to Carbocyclic Nucleosides: Asymmetric Synthesis of 1592U89, a Potent Inhibitor of HIV Reverse Transcriptase.
K. Hammer et al, Tetrahedron 53, (month unavailable) 1997, pp. 5925–5936, Synthesis of Conformationally Restricted Serine Derivatives Through Ruthenium (II)–Catalyzed Ring Closing Metathesis.
A.W. Stumpf et al, J.Chem. Soc., Chem. Commun., (month unavailable) 1995, pp. 1127–1128, Ruthenium–based Catalysts for the Ring Opening Metathesis Polymerisation of Low–strain Cyclic Olefins and of Functionalised Derivatives of Norbornene and Cyclooctene.
P. Schwab et al, J. Am. Chem. Soc., (month unavailable) 1996, 118, pp. 100–110, Synthesis and Applications of $RuCl_2(=CHR')(PR_3)_2$: The Influence of the Alkylidene Moiety on Metathesis Activity.
R. H. Grubbs et al, "Ring–Closing Metathesis and Related Processes in Organic Synthesis", Accounts of Chemical Research, Bd. 28, Nr. 11, 1995, Seiten 437–476, XP002124360.
M. D. E. Forbes et al, "Solvent–Free Cyclization of Linear Dienes Using Olefin Metathesis and The Thorpe–Ingold Effect", J. Am. Chem. Soc., Bd 114, 1992, Seiten 10978–10980, XP002124361.

* cited by examiner

*Primary Examiner*—Gary Geist
*Assistant Examiner*—Taylor V. Oh
(74) *Attorney, Agent, or Firm*—Joseph C. Gil; Diderico van Eyl

(57) ABSTRACT

Using the process according to the invention, it is possible to provide, with few reaction steps, a novel route to α-substituted ring systems, which optionally have further substituents.

8 Claims, No Drawings

PROCESS FOR SYNTHESIZING α-SUBSTITUTED RING SYSTEMS

BACKGROUND OF THE INVENTION

The background of the invention relates to the synthesis of substituted ring systems. Using the process according to the invention, it is possible to provide, with few reaction steps, a novel route to α-substituted ring systems which optionally have further substituents. Cyclohexen-3-ol is an excellent example of a compound which can be prepared according to the invention. It is an important intermediate, for example for preparing Nylon® or Dralon® (from cyclohexanone and ε-caprolactam) and for the synthesis of fine chemicals.

Cyclohexanone and, by hydrogenation, cyclohexanol (of so-called KA oil which is used as a precursor for polymers such as Nylon® and Dralon®) can be obtained from cyclohexen-3-ol by catalytic isomerization, i.e., free from further by-products or subsequent products. Additionally, phenol is obtainable by catalytic dehydrogenation and cyclohexadiene by catalytic dehydration.

Hitherto, cyclohexen-3-ol was obtained by selective hydrogenation of phenol. This process comprises a large number of steps or partial steps. Thus, it is first necessary to produce phenol from benzene, usually by the so-called cumene process in which, in a Friedel-Crafts alkylation, isopropylbenzene is obtained from benzene. A disadvantage of this step is the high expense since this step cannot be carried out catalytically. Correspondingly large amounts of compounds such as iron salts, which either have to be disposed of or worked up, are formed in the Friedel-Crafts alkylation. With the aid of oxygen, this product is subsequently rearranged into phenol and acetone. As a general principle, the co-product acetone is generated in this process. The phenol which has been obtained in this manner is subjected to selective hydrogenation which is stopped at the stage of the cyclohexen-3-ol. Accordingly, this process is expensive, generates large amounts of waste products which are difficult to recycle. Additionally, the process also generates the by-product acetone, which is not always desired. A review is given, for example, by K. Weissermel and H.-J. Arpe in "Industrielle Organische Chemie", 4th Edition, 1994, VCH Verlagsgesellschaft Weinheim, pp. 375–379.

There was therefore a need to develop a process which improves the preparation of (α-substituted ring systems such as cyclohexen-3-ol from easily obtainable starting materials, with a simultaneous reduction in costs.

In principle, the olefin metathesis (a description of this reaction type is given, for example, in M. Schuster, S. Blechert, Angew. Chem. 1997, 109, 2124 and S. Armstrong, J. Chem. Soc., Perkin Trans. 1, 1998, 371), could be considered to be a feasible route for the synthesis of cyclohexen-3-ol and other α-substituted cycloolefins of the same or a greater ring size. The dienes required as starting materials are easily obtainable by the so-called telomerization reaction or by other reaction routes known per se.

By olefin metathesis of functionalized terminal dienes, it is easily possible to obtain various products catalytically by inducing a ring closure of the diene, and ethylene is obtained as a further product of value in this reaction. However, the prior art does not disclose any generally applicable specifications for carrying out certain syntheses.

SUMMARY OF THE INVENTION

The invention relates to a process for preparing at least α-substituted ring systems of the formula (II)

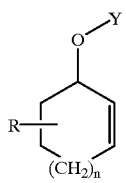

(II)

in which

Y represents a component selected from hydrogen, acyl, alkyl and aryl, sulfonyl, R represents one or more further substituents and n represents the numbers 1, 2, 3 or 4, and where even the double bond may be substituted by at least one radical R. The process involves subjecting a compound of the formula (I)

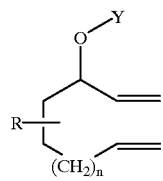

(I)

in which Y, R and n are each as defined above, to a metathesis reaction in the presence of a noble metal catalyst, characterized in that the reaction is carried out in a solvent selected from at least one member of a group consisting of secondary alcohols, tertiary alcohols, trihalogenomethane compounds, supercritical carbon dioxide and ethyl phenyl acetate. These and other features, aspects, and advantages of the present invention will become better understood with reference to the following description and appended claims.

DESCRIPTION OF THE INVENTION

The process according to the invention is based on starting materials which can preferably be obtained from a telomerization reaction (T. Prinz, W. Keim, B. Drießen-H ölscher, Angew. Chem. 1996, 108, 1835; see also, for example, K. Kaneda, H. Kurosaki, M. Terasawa, T. Imanaka, S. Teranishi, J. Org. Chem. 1981, 46, 2356; R. M. Manyik, K. E. Atkins, W. E. Walker, J. Chem. Soc. D. 1971, 7, 330. Alternative synthesis routes for these have also been described or can easily be conceived. The starting materials are easily obtainable, for example by reacting a nucleophile such as water or ammonia with optionally substituted butadienes. This also provides access to other α-substituted cycloolefins besides cyclohexen-3-ol.

In the field of the cycloolefination by metathesis, the synthesis of a cyclopentenol unit in a complex precursor molecule of a natural product has already been disclosed, where the following structure was synthesized under the following conditions (M. T. Crimmins, B. W. King, J. Org. Chem. 1996, 4192):

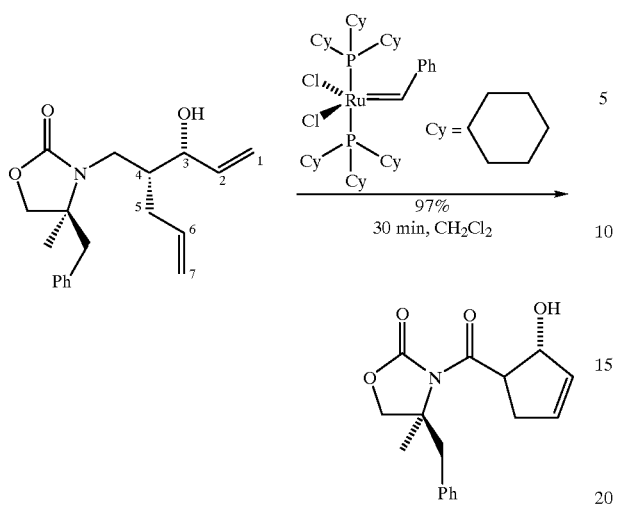

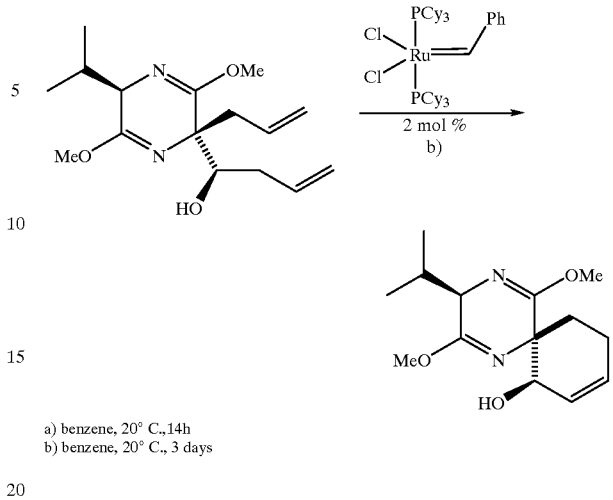

a) benzene, 20° C., 14h
b) benzene, 20° C., 3 days

However, the stated reaction conditions cannot be applied to the synthesis of 2-olefins having larger rings. It was found that for the synthesis of cyclohexenol building blocks as precursors for the synthesis of optically pure amino acids other conditions were required. Moreover, the conditions differ in the reaction time required when changing from the S to the R enantiomer (K. Hammer, K. Undheim, Tetrahedron 1997, 53, 5925). To achieve the stated Yield (88 and 89%, respectively), the solvent benzene which was used had to be added in large amounts. Thus, the reaction was carried out at very high dilution using a solvent which can no longer be commercially employed in these amounts. The dilution used in this process is 5- to 10-times higher than that used in the process according to the invention.

It was found that benzene was not suitable anyway for the synthesis of cyclohexenol since the conversion is not complete. Using the conditions described, the maximum yield was 60%. A rearrangement to the ketone (isomerization allyl alcohol-ketone) was observed as a side reaction. This took place increasingly under the conditions and in the solvents which were given at the very place for formation of the five-membered ring (in dichloromethane) or seven-membered ring (dichloroethane).

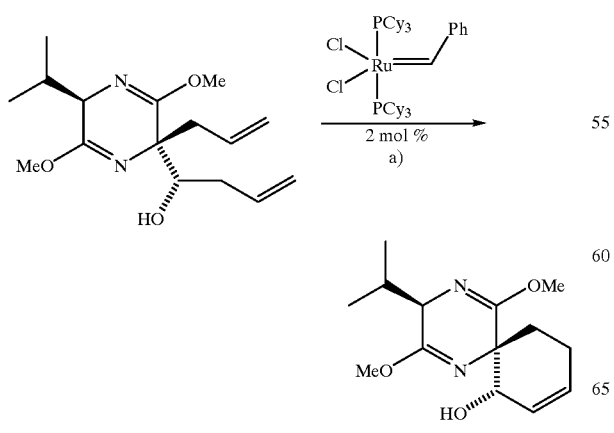

Thus, it is not possible to apply the above example to the synthesis of six-membered or larger rings which are not of the same type as those above.

With respect to compounds having unprotected functional groups, such as in the above case of the 3-hydroxy-1,7-octadiene, the reaction conditions known from the literature do not allow the reaction conditions which are suitable for the reaction described above to be inferred.

It was therefore also an object of the present invention to provide a universally applicable process which also provides, in addition to cyclohexen-3-ol, access to other, optionally larger, α-functionalized unsaturated ring systems of the formula (II):

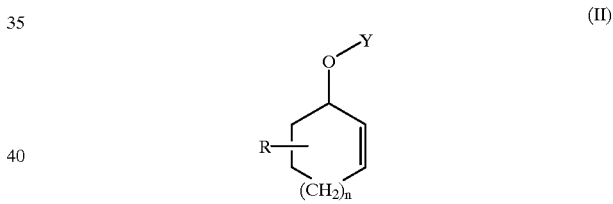

Here, in each case independently of one another,
Y represents a component selected from hydrogen, acyl, alkyl, aryl and sulfonyl,
R represents one or more further substituents, preferably a component selected from hydrogen, optionally fused aryl, alkyl, —CN, —COOR$^1$,

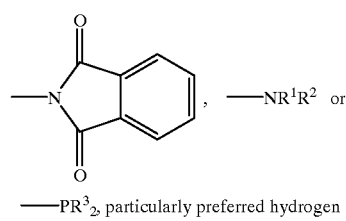

, —NR$^1$R$^2$ or

—PR$^3{}_2$, particularly preferred hydrogen in which
R$^1$ represents a component selected from alkyl, aryl, hydrogen,
R$^2$ represents formyl, acetyl, acyl, sulfonyl, carboxyalkyl or -aryl,
R$^3$ represents a component selected from alkyl, phenyl and n represents the numbers 1, 2, 3 or 4, preferably 1 or 2, and most preferably 1.

The double bond in the compound (II) may likewise be substituted by at least one radical R.

The nature of the substituent R is not essential for the invention. In principle, all radicals which are customary in organic chemistry can be used. Preferred alkyl groups R according to the invention are linear or branched $C_1$- to $C_8$-alkyl groups, particularly preferably linear $C_1$- to $C_4$-alkyl groups. The aryl groups Y and R are preferably phenyl groups.

Surprisingly, it has been found that the choice of solvent in the process according to the invention is critical for the success of the reaction. More particularly, it was found that, depending on the choice of solvent, side reactions may occur. These side reactions consist in an isomerization of the allyl alcohol to the corresponding ketone or in an oxidation to the corresponding enone system (see reaction scheme below). Only in a few solvents is it possible to suppress these side reactions efficiently. In some solvents, such as 1,2-dichloroethane or 1,1,1-trichloroethane or even dichloromethane, these side reactions occur almost quantitatively when the synthesis of the ring systems to be prepared according to the invention is attempted. Suitable in principle for the process according to the invention are, for example, ethyl phenyl acetate or even supercritical $CO_2$, but the reaction rates are in particular in the latter case very slow, which makes them appear to be less preferred for commercial use.

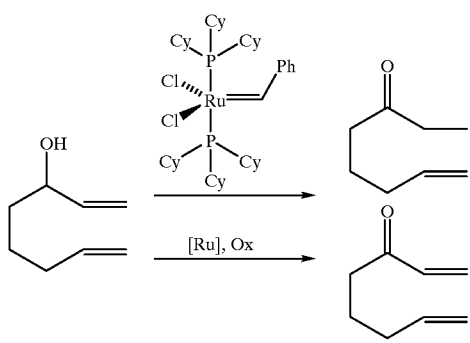

Consequently, it is preferred to use the solvents listed below. The use of secondary alcohols or tertiary alcohols as solvents for the process according to the invention permits yields of from 50% to 80% to be obtained. However, without it being possible to suppress these side reactions completely. Particular preference is given to trihalomethane compounds such as chloroform or bromoform as solvents for carrying out the metathesis reaction according to the invention, i.e., for generating rings having a number of members of >5. Preference is given to using only one solvent and not a mixture. It is not possible to carry out this reaction neat.

In the olefin metathesis reaction of the process according to the invention, the ring closure is induced using a noble metal catalyst, preferably a ruthenium catalyst. In the process according to the invention, particular preference is given to using, as catalysts, the ruthenium alkylidene compounds described in WO-A-93/20111, the ruthenium-based catalyst systems described by A. W. Stumpf, E. Saive, A. Deomceau and A. F. Noels in J. Chem. Soc., Chem. Commun. 1995, 1127–1128 or the catalyst systems published by P. Schwab, R. H. Grubbs and J. W. Ziller in J. Am. Chem. Soc. 1996, 118, 100. A particularly preferred catalyst is bis(tricyclohexylphosphine)benzylideneruthenium(IV) dichloride. In a preferred embodiment of the process according to the invention, the operations are carried out under a permanent atmosphere of protective gas, so that the catalyst system can be used for a plurality of cycles.

The reaction time varies and depends on the reaction temperature, the reaction pressure and the type and the amount of the catalyst. Usually, the reaction time is from 0.01 to 30 hours, preferably from 1 to 10 hours.

The pressure to be used in the process according to the invention is not a critical parameter. It is also possible to reduce the pressure to 0.1 bar, for example, and to apply pressures of up to 100 bar, for example. However, preference is given to an absolute pressure of from 0.1 to 10 bar, particularly preferably to atmospheric pressure.

The amount of catalyst used in the process according to the invention is generally at from 0.001 to 10 mol %, based on the compound of the formula (I). The reaction is preferably carried out using from 0.1 to 1 mol % of catalyst.

The reaction temperature is not a critical parameter. In general, the reaction temperature is determined by the boiling point of the solvent used or by the boiling points of the starting materials, unless the action of pressure works against this.

The general reaction scheme of the process according to the invention is accordingly:

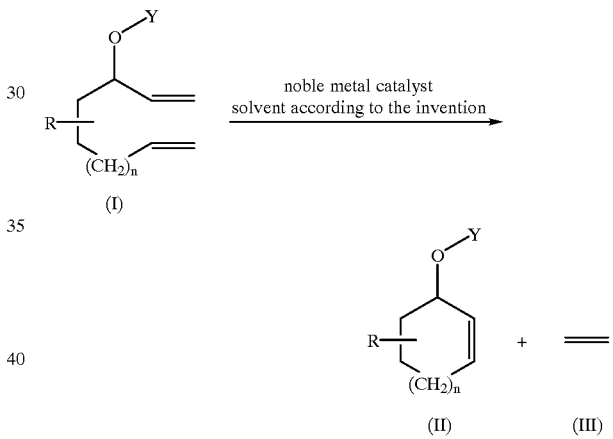

where the meanings of the substituents correspond to the above-mentioned definitions.

The invention provides valuable advantages to the industry. With the process according to the invention, it is now possible to provide, in few reaction steps, a novel route to α-substituted ring systems which optionally have further substituents. Cyclohexen-3-ol, for instance, is an excellent example of a compound which can be prepared according to the invention. Cyclohexen-3-ol is an important intermediate for preparing polymers such as polyamides, e.g., Nylon®, or acrylic fibers, e.g., Dralon® (from cyclohexanone and ε-caprolactam) and for the synthesis of fine chemicals.

The invention is further described in the following illustrative examples in which all parts and percentages are by weight unless otherwise indicated.

EXAMPLES

Example 1

(Cyclohexen-3-ol)

In a Schlenk tube, 63 mg (0.5 mmol) of 3-hydroxy-1,7-octadiene and 17 mg of bis(tricyclohexylphosphine) benzylideneruthenium(IV) dichloride (1.3 mol %) was dissolved in 5 ml of abs. chloroform under an atmosphere of argon. The mixture was allowed to react at 56° C. for 14 h. For work-up, the mixture was filtered through a very short (about 0.5 cm) silica gel filtration column (mobile phase: acetonitrile) and the filtrate was concentrated. Yield of cyclohexen-3-ol: 47 mg (0.48 mmol, 96%). It should be noted that the chloroform did not contain any ethanol (as stabilizer).

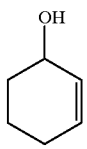

$^1$H NMR (400 MHz, CDCl$_3$) δ 5.75 (1H, d, J=10.0 Hz), 5.70 (1H, d, J=10.0 Hz), 4.18 (1H, s), 3.72 (1H, s), 1.98 (2H, m), 1.84 (1H, m), 1.72 (1H, m), 1.55 (2H, m).

Example 2

(Cyclohexen-3-ol)

In a Schienk tube, 63 mg (0.5 mmol) of 3-hydroxy-1,7-octadiene and 17 mg of bis(tricyclohexylphosphine) benzylideneruthenium(IV) dichloride (1.3 mol %) were dissolved in 5 ml of abs. bromoform under an atmosphere of argon. The mixture was allowed to react at 80° C. for 5 h. For work-up, the mixture was filtered through a very short (about 0.5 cm) silica gel filtration column (mobile phase: acetonitrile) and the filtrate was concentrated. Yield of cyclohexen-3-ol: 48 mg (0.49 mmol, 99%).

Although the present invention ha s been described in detail with reference to certain preferred versions thereof, other variations are possible. Therefore, the spirit and scope of the appended claims should not be limited to the description of the versions contained therein.

What is claimed is:

1. A process for preparing an α-substituted ring system of the formula (II)

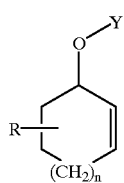

wherein

Y comprises a component selected from the group consisting of hydrogen atoms, acyl groups, alkyl groups, aryl groups, and sulfonyl groups, R represents one or more substituents selected from the group consisting of hydrogen, optionally fused aryl, alkyl, —CN, —COOR$^1$, and a group having the formula

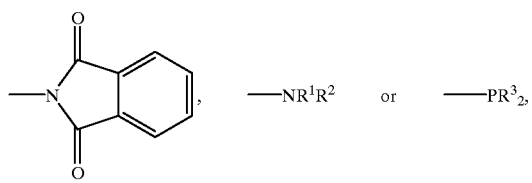

in which

R$^1$ represents a component selected from alkyl, aryl, hydrogen,

R$^2$ represents formyl, acetyl, acyl, sulfonyl, carboxyalkyl or -aryl,

R$^3$ represents a component selected from alkyl, phenyl and n represents the numbers 1, 2, 3 or 4, wherein the double bond may be substituted by at least one radical R;

the process comprising the step of subjecting a compound of the formula (I)

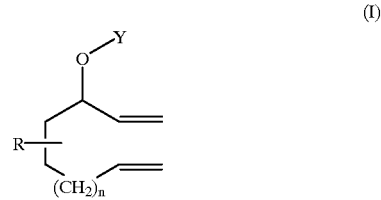

wherein Y, R and n are each as defined above, to a metathesis reaction in the presence of a noble metal catalyst in a solvent comprising a component selected from the group consisting of secondary alcohols, tertiary alcohols, trihalomethane compounds, supercritical carbon dioxide and ethyl phenyl acetate.

2. The process of claim 1, wherein the step of subjecting a compound of the formula (I) to a metathesis reaction occurs in the presence of a noble metal catalyst comprising ruthenium complex.

3. The process of claim 1, wherein the step of subjecting a compound of the formula (I) to a metathesis reaction occurs in the presence of a noble metal catalyst comprising bis(tricyclohexylphosphine) benzylideneruthenium(IV) dichloride.

4. The process of claim 1, wherein the step of subjecting a compound of the formula (I) to a metathesis reaction occurs with a solvent comprising a trihalomethane compound.

5. The process of claim 1, wherein the step of subjecting a compound of the formula (I) to a metathesis reaction occurs with a solvent comprising chloroform.

6. The process of claim 1, wherein the step of subjecting a compound of the formula (I) to a metathesis reaction occurs with a solvent comprising bromoform.

7. The process of claim 1, wherein, in the formulae (I) and (II), Y and R each represent hydrogen and n is 1.

8. The process of claim 1, wherein the step of subjecting a compound of the formula (I) to a metathesis reaction is not carried out neat.

* * * * *